(12) United States Patent
Scharf et al.

(10) Patent No.: US 10,037,676 B1
(45) Date of Patent: Jul. 31, 2018

(54) REMOTE COGNITIVE IMPAIRMENT SCREENING AND LOCATION VERIFICATION SYSTEM AND METHOD

(71) Applicants: David Scharf, Pompano Beach, FL (US); Daniel Sokol, Lighthouse Point, FL (US)

(72) Inventors: David Scharf, Pompano Beach, FL (US); Daniel Sokol, Lighthouse Point, FL (US)

( * ) Notice: Subject to any disclaimer, the term of this patent is extended or adjusted under 35 U.S.C. 154(b) by 18 days.

(21) Appl. No.: 15/096,741

(22) Filed: Apr. 12, 2016

Related U.S. Application Data

(60) Provisional application No. 62/235,790, filed on Oct. 1, 2015.

(51) Int. Cl.
*G08B 23/00* (2006.01)
*G08B 21/18* (2006.01)
*H04W 4/02* (2018.01)
*G06F 8/61* (2018.01)

(52) U.S. Cl.
CPC ............ *G08B 21/182* (2013.01); *G06F 8/61* (2013.01); *H04W 4/02* (2013.01)

(58) Field of Classification Search
None
See application file for complete search history.

(56) References Cited

U.S. PATENT DOCUMENTS

| | | | |
|---|---|---|---|
| 5,137,345 A | 8/1992 | Waldorf et al. | |
| 5,187,506 A | 2/1993 | Carter | |
| 5,692,502 A | 12/1997 | Alpert | |
| 7,394,392 B1 | 7/2008 | Roe | |
| 7,473,233 B2 | 1/2009 | Crucilla | |
| 7,619,533 B2 | 11/2009 | Crucilla | |
| 8,317,328 B1 | 11/2012 | Harris | |
| 8,761,360 B1 | 6/2014 | Gongaware et al. | |
| 8,899,748 B1 | 10/2014 | Migdal | |
| 8,903,060 B2 | 12/2014 | Gongaware et al. | |
| 8,971,590 B2 | 3/2015 | Britz et al. | |
| 9,002,067 B2 | 4/2015 | Siilats | |
| 2010/0204600 A1 | 8/2010 | Crucilla | |
| 2012/0238831 A1 | 9/2012 | Benford | |

(Continued)

*Primary Examiner* — Brian Zimmerman
*Assistant Examiner* — Kevin Lau
(74) *Attorney, Agent, or Firm* — Mark D. Bowen; Malin Haley DiMaggio & Bowen, P.A.

(57) ABSTRACT

A system and method for monitoring and screening individuals subject to voluntary or mandatory personal conduct restrictions, such as prohibitions on alcohol and drug use, as well as geographic travel limitations using remote wireless communications and smartphone technology. A computer software program, including a Client Module and a downloadable Subject Module is preferably provided as part of the system to facilitate the execution of the method. Biometric verification of the Subject's identity is achieved via wireless communication from the subject to the Client. A comparison of a first facial photograph obtained from the subject in a known, non- impaired condition with a current facial photograph obtained from the subject and wirelessly transmitted to the client provides a basis for determining a probability of cognitive impairment. GPS data obtained from the Subject's smartphone enables compliance with travel requirements.

4 Claims, 3 Drawing Sheets

(56) References Cited

U.S. PATENT DOCUMENTS

| | | | |
|---|---|---|---|
| 2013/0167226 A1 | 6/2013 | Lin | |
| 2015/0123787 A1* | 5/2015 | Watson | G08B 21/0415 340/539.13 |
| 2016/0161468 A1* | 6/2016 | Keays | G01N 33/4972 73/23.3 |
| 2016/0182850 A1* | 6/2016 | Thompson | H04N 9/8205 348/158 |
| 2016/0318521 A1* | 11/2016 | Nothacker | B60W 40/08 |
| 2017/0049362 A1* | 2/2017 | Macknik | A61B 5/1104 |

* cited by examiner

REMOTE COGNITIVE IMPAIRMENT SCREENING AND LOCATION VERIFICATION SYSTEM AND METHOD

CROSS REFERENCE TO RELATED APPLICATIONS

This application claims the benefit of provisional U.S. Patent Application Serial No. 62/235,790, filed on Oct. 1, 2015.

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all rights whatsoever.

BACKGROUND OF THE INVENTION

1. Field of the Invention

The present invention relates to the detecting impairment in monitored subjects, and more particularly, to a random cognitive impairment screening system and method using a subject's smartphone to verify the subject's identification, location, and a visual indication of potential impairment.

2. Description of Related Art

Restrictions on personal conduct and travel are often placed on individuals, sometimes voluntarily and other times involuntarily. For example, professional athletes often sign large contracts containing stipulations and conditions governing the athletes conduct. These so called personal conduct provisions may include a wide variety of conduct limitations, including prohibiting the athlete from consuming alcohol or illegal drugs, prohibiting the athlete from visiting certain locations, imposition of curfew restrictions, as well as travel restrictions, limitations, and/or requirements.

Verifying compliance with personal conduct restrictions, mandates, and prohibitions, presents difficulties. For example, one common restriction placed on, or voluntarily accepted by, individuals is a prohibition from consuming alcohol or drugs. Verifying whether an individual has violated such a prohibition typically requires the person to submit to alcohol and/or drug testing in order to confirm compliance. This typically entails arranging for the individual to appear at random and/or pre-arranged times in order to provide a blood and/or urine sample for analysis. This method of verification is costly and time-consuming, both for the monitored individual as well as monitoring personnel. Other conduct restrictions, such as travel and curfew restrictions pose similar compliance verification difficulties.

The background art reveals a number of attempts directed to enhancing and improving the monitoring of individuals subject to personal conduct restrictions. For example, U.S. Pat. No. 5,137,345, issued to Waldorf et al., discloses a table-top apparatus configured to surround the eyes for monitoring physiological responses for detecting the presence of drug impairment. U.S. Pat. No. 5,187,506, issued to Carter, discloses portable scanning pupillometers for detecting worker impairment. U.S. Pat. No. 8,317,328, issued to Harris et al., discloses a device for administering a gaze nystagmus field sobriety test. The device may comprise a portable computing device, such as a smartphone. U.S. Pat. No. 8,899,748, issued to Migdal, discloses a system for detection of eye nystagmus in a test subject using a camera to capture a series of sequential digital images of the test subject's face, and analyzing the images to determine blood alcohol concentration.

Streetime Technologies, LLC, maker of an eye-based self-administered prescreening system has a published patent application (Pub. No. U.S. 2010/0204600) for an Apparatus and Method for Passive Testing of Alcohol and Drug Abuse. That system includes a drug testing home device or a drug testing kiosk device for use by the participant. Participants are enrolled with biometric identification (fingerprints, voice prints, images) which are validated prior to a test. The system conducts and analyzes the test to determine whether the participant has been using alcohol or other drugs and should be subjected to a confirming urinalysis exam. The test primarily comprises a breathalyzer, but may further check for drugs using a volatile organic compound gas sensor and a pH sensor.

A smartphone-based, GPS monitoring system is available from Telmate LLC under the trademark TELMATE GUARDIAN®. The Telmate system prompts released offenders to periodically check-in and speak a random series of numbers while multiple photos are taken. The voice recording and photos are used to determine a positive match, and the offender's smartphone automatically reports its location. Browser-based mapping software tracks, logs, and compares the GPS location data against the individual's custom parameters.

The above-referenced advancements in the art of impairment detection are burdened by a number of limitations and disadvantages that prevented widespread use and acceptance. One significant disadvantage with the impairment screening systems of the background art involves the reliance on expensive and complex specialized hardware.

BRIEF SUMMARY OF THE INVENTION

The present invention overcomes the limitations and disadvantages present in the art by providing a system and method for verifying compliance with personal conduct restrictions and prohibitions. The system is employed by a compliance monitoring and verification entity (hereafter "Client") vested or charged with the right to monitor an individual who is subject to personal conduct restrictions (hereinafter "Subject"). A computer software program, including a Client Module and a downloadable software application (i.e. an "App"), identified as the Subject Module, are provided to facilitate the execution of the impairment verification methods. The process is initiated with the Subject downloading the Subject Module App ("SMA") to his smartphone. Once downloaded, the Subject launches the SMA to set-up and enroll in the system. The enrollment and set-up process requires that the Subject provide a biometric registration sample, such as a face image, voice sample, fingerprint, or retinal scan, or combination thereof, which will be later used to confirm the identity of the Subject. In addition, the Subject provides at least one non-impaired baseline image of the Subject's face using the smartphone camera function. Furthermore, the App utilizes the GPS location capabilities present in the Subject's smartphone to monitor the Subject's movement and location.

Upon completion of the enrollment procedure, the Client may establish wireless communication with the Subject, via the Subject's smartphone, at any time on a random basis with an impairment screening test request. In response to the request, the Subject must first verify his identity by using his smartphone to provide a biometric sample, which may comprise a suitable biometric sample corresponding to the biometric registration sample, such as face, voice, fingerprint, or retinal scan, or combination thereof. The Subject is prompted to undergo impairment screening by using the smartphone camera to capture one or more images of his face. The image(s), along with GPS location data, is transmitted to the Client where the image data is processed and analyzed to determine whether the Subject appears impaired. The analysis concludes with a determination of probable impairment or probable non-impairment. The Subject is informed of the results, and if the analysis indicates probable impairment, the Subject will be provided instructions to undergo more detailed analysis, which may involve the subject submitting to a urinalysis, breathalyzer, or other suitable test.

In accordance with another significant aspect of the present invention, GPS location data may be periodically and/or continuously obtained by the Client from the Subject's smartphone. The obtained GPS data is compared by the Client Module to verify whether the Subject is in compliance with predetermined location and/or travel restrictions or requirements. Alerts may be generated, for example, is the Subject travels to a prohibited location, travels beyond a certain radius, or fails to travel to a scheduled predetermined location.

Another significant aspect of the present invention relates to architecture designed to defeat attempts by the Subject to circumvent the impairment detection and/or location detection aspects of the present invention. In accordance with this aspect, if the Subject turns the GPS location function "off", or the system otherwise is unable to obtain the Subject's GPS location, an alert may be generated by the Client Module notifying monitoring personnel that the system has lost the Subject's GPS location. In response, the system attempts to gather information from the Subject's smartphone, such as by remotely activating the camera and/or microphone features to obtain video (or photographic) images from the phone along with sound clips which may be useful in identifying the Subject's location. These functions are preferably embedded within the Subject Module App. so as to be automatically triggered if, for example, the Subject turns the GPS feature "off." In addition, the SMA is preferably adapted with a function that can disable the Subject's smartphone in situations wherein the Subject fails to comply with monitoring stipulations.

Accordingly, it is an object of the present invention to provide advancements in systems and methods directed to compliance verification for individuals subject to personal conduct restrictions.

Another object of the present invention is to provide advancements in self-administered impairment screening without requiring specialized, costly, and complex screening hardware.

Still another object of the present invention is to provide advancements in the field of remote impairment screening of individuals using common smartphone technology.

Yet another object of the present invention is to provide a system and method for monitoring the movement and location of an individual who is subject to travel restrictions and limitations.

In accordance with these and other objects, which will become apparent hereinafter, the instant invention will now be described with particular reference to the accompanying drawings.

BRIEF DESCRIPTION OF THE SEVERAL VIEWS OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

Figure 1:
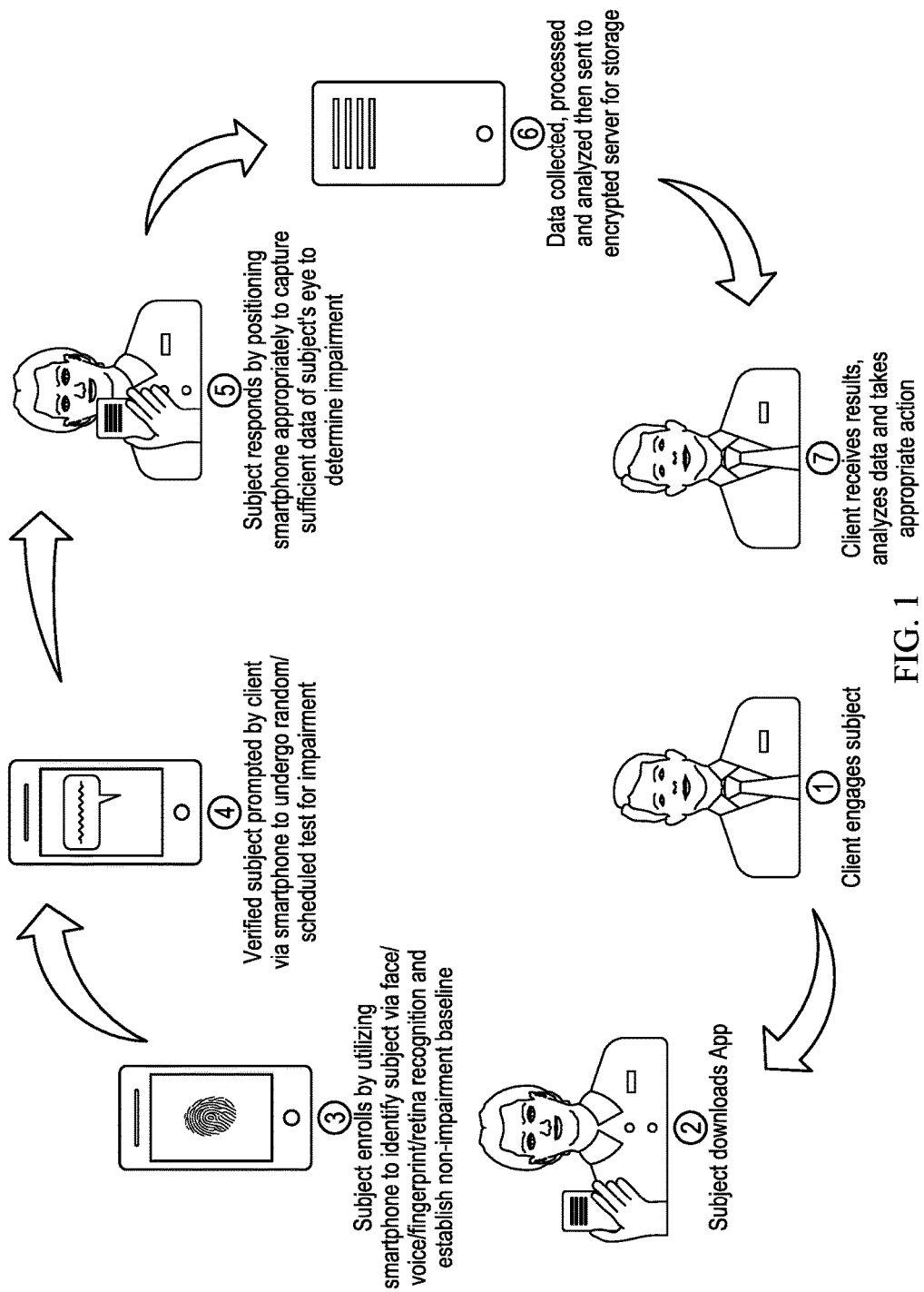
FIG. 1 is a flow chart illustrating an impairment screening system and method in accordance with the present invention.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms may be provided. A recital of one or more synonyms does not exclude the use of other synonyms, The use of examples anywhere in this specification including examples of any terms discussed herein is illustrative only, and in no way limits the scope and meaning of the invention or of any exemplified term. likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control. As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated. As used herein, when a number or a to range is recited, ordinary skill in the art understand it intends to encompass an appropriate, reasonable range for the particular field related to the invention. The term "his" shall be broadly construed to encompass male and female individuals, including children, adults, and senior citizens.

Turning now to the drawings, FIGS. 1-4, illustrate a system and method, generally referenced as 10, for monitoring individuals who are subject to personal conduct restrictions, particularly including prohibitions on the consumption of drugs and alcohol and travel mandates and restrictions. Computer software is provided to facilitate execution of the methods disclosed herein. The computer software includes a Client Module which functions as an administrative software program and database management system. As used herein the term "Client Module" shall broadly be construed to mean an administrative software program and/or database management program that receives and organizes data relating to an enrolled Subject. In a preferred embodiment, the Client Module resides on a computer system server maintained by the Client (e.g. entity charged with monitoring one or more Subjects). The Client Module functions to establish accounts for monitored Subjects by receiving and storing input data relating to the Subjects. Such data may typically include the Subject's name, address, cell phone/smartphone number, and travel restrictions. Examples of travel restrictions may include restrictions that prohibit the Subject from visiting certain commercial establishments (e.g. Gentlemen's clubs), or from traveling to certain geographic locations (e.g. local entertainment districts), or other travel restrictions that prohibit travel beyond a certain radius. Examples of travel mandates may include requiring the Subject to adhere to a curfew, or to be at a specified place (e.g. workout or therapy) at a specified day and time.

The computer software further includes a downloadable software application or App, referred to as the Subject Module App ("SMA"), adapted for downloading to the Subject's smartphone. The SMA functions as the interface between the Subject and the Client via the Client Module. In accordance with the method of the present invention, the preliminary step of having the Subject download the SMA into his smartphone configures the smartphone as an integral, wireless-enabled, device for use in impairment screening and location verification in accordance with the present invention. After downloading the SMA, a set-up/enrollment process is performed.

In accordance with a first method step, referenced as 1, the Client initially establishes wireless communication with the Subject via the Subject's smartphone to initiate the set-up/enrollment process. In accordance with a second method step, referenced as 2, the Subject wirelessly downloads the SMA which functions as the Subject's interface with the system. In accordance with a third method step, referenced as 3, the Subject enrolls in the system by providing a biometric registration sample which will be used for identification verification, and completes the enrollment process by capturing one or more photographs of his face using the smartphone camera thereby establishing a non-impaired baseline. The enrollment process requires that the Subject provide a biometric registration sample as direct input to the smartphone. The biometric registration sample may comprise: a face image; voice sample; fingerprint scan; or retinal scan; or any combination thereof. The registration sample is wirelessly transmitted from the Subject's smartphone to the Client for archival storage in a database, and will later be used to confirm the identity of the Subject. As noted above, the Subject provides at least one non-impaired baseline image of the Subject's face using the smartphone camera function, which image is wirelessly transmitted to the Client for archival storage in a database. As should be apparent, the Subject's smartphone is used to obtain the requisite biometric registration sample depending on the biometric parameter selected for identification verification.

In accordance with a fourth method step, referenced as 4, the Client contacts the previously enrolled Subject, via wireless communication, and transmits an Impairment Test Notification ("ITN") to the Subject's smartphone. The ITN prompts the Subject to undergo either a random or scheduled impairment screening test. The ITN may be transmitted by text, e-mail, or telephone call, or any other suitable wireless notification method. Further, the test is preferably self-administered immediately after receipt of the notification so as to capture the Subjects present state of impairment or non-impairment. The Subject may be required to self-administer the impairment test within a predetermined amount of time, such as 60 seconds, 5 minutes etc. Further, the system may be configured to require routine (e.g. daily) impairment tests on a preplanned/prescheduled repeating basis. In that case, ITN's may still be transmitted per the predetermined schedule.

As illustrated in the method step referenced 5, and in accordance with a preferred embodiment, the Subject is screened/tested for impairment by obtaining information about the Subject using the Subject's smartphone. In response to the ITN, the Subject must first verify his identity by using his smartphone to provide an identification-verifying biometric sample (or verification sample), which may comprise a suitable biometric sample corresponding to the biometric registration sample, such as face, voice, fingerprint, retinal scan, or combination thereof. The verification biometric sample is transmitted to the Client for comparison with the biometric registration sample in order to verify the identity of the Subject. The Subject is further prompted to undergo impairment screening by using the smartphone camera to capture one or more impairment verification images of the Subject's face, with particular emphasis on the Subject's eyes which are known to indicate impairment.

In accordance with method step 6, the image(s), along with GPS location data, is transmitted by the SMA to the Client where the image data is processed and analyzed to determine whether the Subject appears impaired, the analysis concluding with a determination of probable impairment or non-impairment. More particularly, the impairment verification image is transmitted to the Client for comparison to the non-impaired baseline image and analysis seeking indications of impairment, probable impairment, or possible impairment, any of which may trigger a call for further impairment screening.

In accordance with method step 7, the Client analyzes the results and takes appropriate action. The Subject is informed of the results by wireless transmission of an "impairment verification results" message from the Client Module to the Subject via the Subject Module. If the analysis indicates probable impairment, the message further provides suitable instructions to the Subject for follow-up. For example, the Subject may be instructed to undergo more detailed analysis, which may involve the subject submitting to a urinalysis, breathalyzer, or other suitable test.

Figure 2:
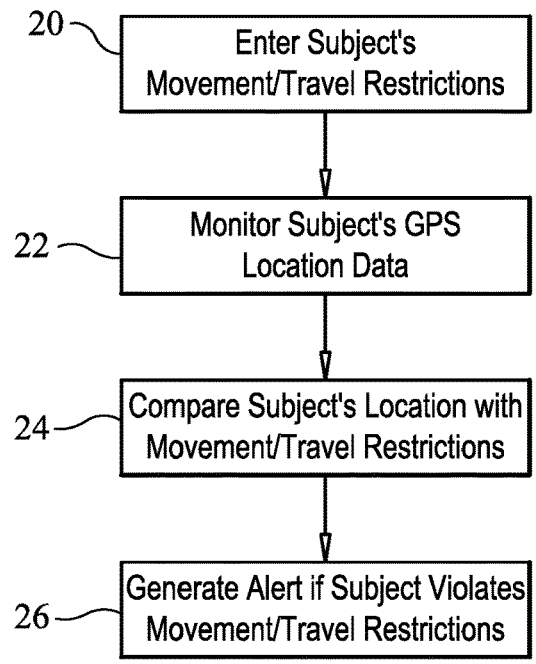
FIG. 2 is a flow chart illustrating verification of the Subject's movement/travel restrictions using smartphone GPS data.

As illustrated in FIG. 2, a further significant aspect of the present invention relates to monitoring the movement and location of the Subject using GPS data obtained from the Subject's smartphone. In accordance with this aspect of the present invention, the present invention functions to verify compliance with personal conduct provisions, including any geographical movement or travel restrictions. Any restrictions on the Subject's movement and/or travel are entered into the Client Module as either prohibitions or limitations relating to travel, as illustrated by step 20. These prohibitions and limitations may include requiring that the Subject be at a location during prescribed times (i.e. Subject must be at home after 10:00 PM), or restrictions (i.e. Subject is prohibited from visiting the nightclub district of town), or client may not travel more than 20 miles from home, or any other suitable position-based limitations. GPS location data may be periodically and/or continuously obtained by the Client from the Subject's smartphone as illustrated by step 22. The obtained GPS data is compared by the Client Module with the previously entered movement/travel restriction data to verify whether the Subject is in compliance therewith as illustrated by step 24. Finally, an alert is generated when the GPS data indicates that the Subject is not in compliance with movement/travel restrictions.

Figure 3:
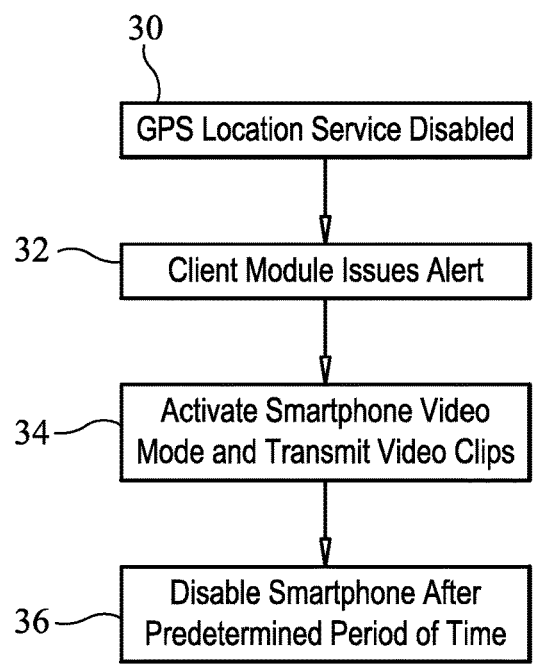
FIG. 3 is a flow chart illustrating evidence gathering features employed if the Subject attempts to circumvent the impairment detection and/or location detection aspects of the present invention.

As illustrated in the flowchart of FIG. 3, another significant aspect of the present invention relates to architecture designed to defeat attempts by the Subject to circumvent the impairment detection and/or location detection aspects of the present invention. In accordance with this aspect, if the Subject turns the GPS location function "off", or the system otherwise is unable to obtain the Subject's GPS location, as illustrated in step 30, an alert may be generated by the Client Module notifying monitoring personnel that the system has lost the ability to verify the Subject's GPS location as illustrated in step 32. In response, the system may attempt to gather information from the Subject's smartphone activating the camera and/or microphone features to obtain video (or photographic) images from the phone along with sound clips which may be useful in identifying the Subject's location as illustrated in step 34. These functions are preferably embedded within the Subject Module App and are automatically triggered if, for example, the Subject turns the GPS location function "off." The system is further capable disabling the Subject's smartphone, after a predetermined period of time, should the GPS location function remain "off" as illustrated in FIG. 36. In addition, other non-compliance steps, such as suspending access to credit cards and bank accounts are contemplated remedies for non-compliance.

Figure 4:
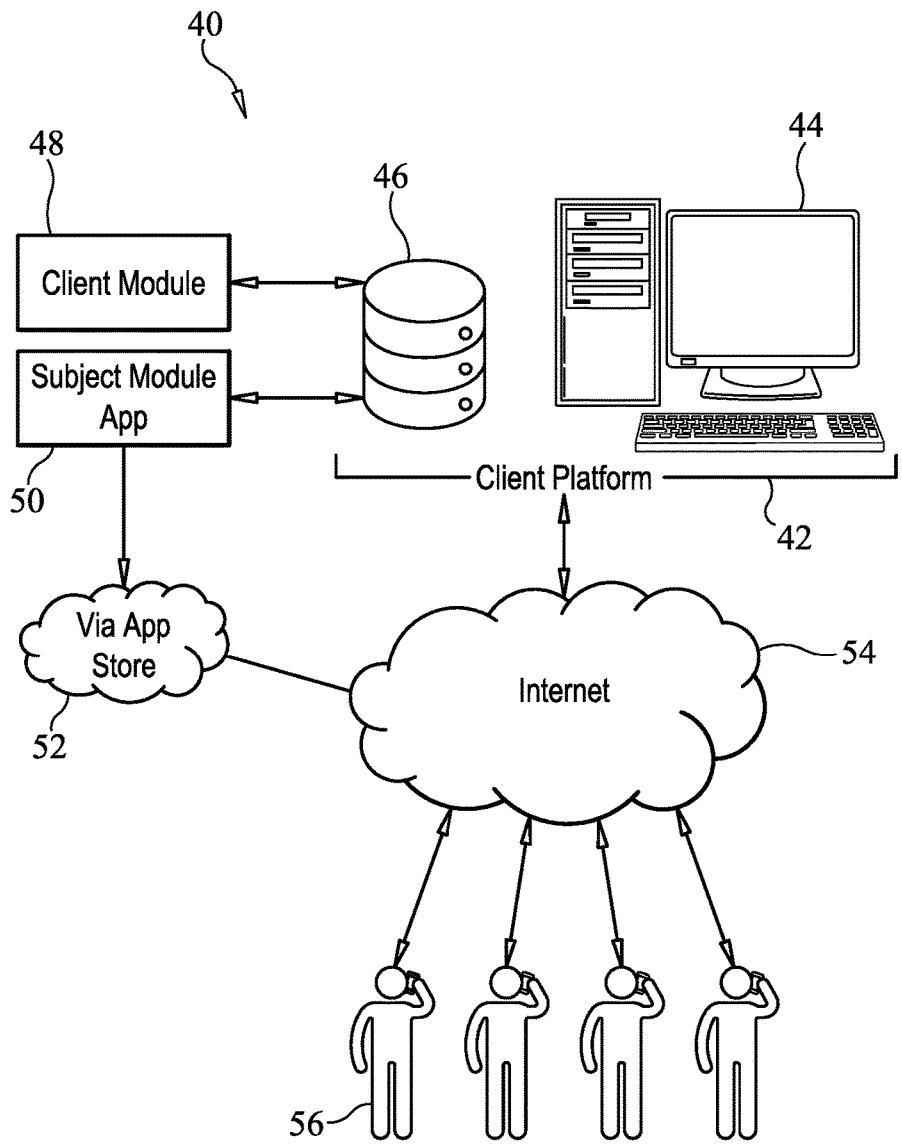
FIG. 4 is a schematic system diagram for the impairment screening system of the present invention.

FIG. 4 provides a schematic illustration of a system, generally referenced as 40, in accordance with the present invention. A client computer platform, generally referenced as 42, includes a computer system 44 and a data storage device 46. The Client Module computer program 48 is illustrated along with the Subject Module App 50. It should be noted, however, that the exact storage location of each of the Client Module and Subject Module App may vary without departing from the scope of the invention. The Subject Module App is stored so as to be available for wireless download, such as from an App store 52, via the Internet 54 as is known in the art. The system of the present invention may be used to monitor and screen a plurality of Subjects, referenced a 56, to screen for impairment and/or to monitor personal conduct provisions.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. A system for remote monitoring and cognitive impairment screening of a Subject person by a screening entity, said system including:

a client computer platform including a computer processor and data storage device;

a client module computer software program stored on said data storage device;

a downloadable computer software application package;

a smartphone having said downloadable computer software application stored thereon;

said client module configured to wirelessly enroll the Subject by wirelessly receiving a biometric registration sample and a non-impaired baseline photographic still image of at least one of the Subjects eyes obtained from the Subject using said smartphone;

said client module configured to maintain Subject-specific data including said biometric registration sample, said non-impaired baseline image of said at least one of the Subject's eyes, and personal conduct provisions;

an impairment test notification generated by said client module and wirelessly transmitted to said smartphone;

a biometric verification sample obtained from the Subject using said smartphone and wirelessly transmitted to said client computer platform;

an impairment verification image of at least one of the Subject's eyes obtained from the Subject using said smartphone and wirelessly transmitted to said client computer platform;

an impairment verification results message including the results of an impairment test based on a visual comparison of said non-impaired baseline image with said impairment verification image, said impairment verification results message wirelessly transmitted to said smartphone;

said client module further including personal conduct provisions for the Subject, said personal conduct provisions including at least one provision selected from the group of: (i) a geographic location restriction provision prohibiting travel to one or more locations based date and/or time; (ii) a geographic location restriction provision restricting travel to within a predetermined radius based on date and/or time; or, (iii) a geographic location mandate provision requiring travel to one or more locations based on date and/or time;

said client module periodically receiving GPS location data wirelessly received from the Subject's smartphone, and generating an alert when the GPS data indicates that the Subject is not in compliance with one of said personal conduct provisions.

2. The system of claim 1, further including the remote activation, by said client module, of at least one of the Subject's smartphone audio recording feature to record an audio file in response to said alert, and automatic wireless transmission of audio file from said smartphone to said client module.

3. The system of claim 1, wherein said client module transmits a signal disabling the Subject's smartphone in response to said alert.

4. A wireless method for remote cognitive impairment screening of a Subject person by a screening entity, said method including the steps of:

providing computer software including a client module and a downloadable subject module;

installing said client module on a client computer system;

downloading said subject module to a smartphone possessed by the Subject;

obtaining a biometric registration sample from the Subject using said smartphone;

transmitting said biometric registration sample to said client for storage on said client computer system;

obtaining a baseline photographic image of at least one of the Subject's eyes when the subject is not cognitively impaired using said smartphone;

transmitting said baseline photographic image to said client for storage on said client computer system;

wirelessly contacting said Subject via said smartphone and prompting said Subject to perform an impairment screening test;

obtaining a biometric verification sample from said Subject using said smartphone;

obtaining at least one impairment verification still image of at least one of the the Subject's eyes using said smartphone;

wirelessly transmitting said biometric verification sample and said at least one impairment verification image to said client;

verifying the identity of the Subject by comparing said biometric verification sample with said biometric registration sample;

determining whether the Subject appears impaired by visually comparing said baseline photographic image with said screening photographic image;

programming said client module with personal conduct provisions for the Subject, said personal conduct provisions including at least one provision selected from the group of: (i) a geographic location restriction provision prohibiting travel to one or more locations based date and/or time; (ii) a geographic location restriction provision restricting travel to within a predetermined radius based on date and/or time; or, (iii) a geographic location mandate provision requiring travel to one or more locations based on date and/or time generating periodic wireless transmissions of GPS location data from said smartphone to said client platform;

generating an alert when said GPS location data deviates from said personal conduct provisions; and remotely activating at least one of the Subject's smartphone audio recording features in response to said alert, recording an audio file, and wirelessly transmitting said audio file from said smartphone to said client module.

\* \* \* \* \*